United States Patent [19]

Miyazaki et al.

[11] Patent Number: 5,435,892
[45] Date of Patent: Jul. 25, 1995

[54] PROCESS FOR SEPARATING METHANOL AND METHYL ACRYLATE OR METHYL METHACRYLATE

[75] Inventors: Seiji Miyazaki; Yasutaka Nakashima; Toshihiro Satoh, all of Hiroshima; Tadao Ida, Ishikawa; Etsuji Sato; Akio Tani, both of Osaka, all of Japan

[73] Assignees: Mitsubishi Rayon Co., Ltd.; Osaka Organic Chemical Ind. Co., Ltd., both of Japan

[21] Appl. No.: 113,135

[22] Filed: Aug. 30, 1993

[51] Int. Cl.$^6$ .................................................. B01D 3/34
[52] U.S. Cl. .................................... 203/95; 203/97; 203/98; 203/DIG. 9; 203/DIG. 21; 203/DIG. 23; 560/218; 568/913
[58] Field of Search ................... 203/95, 14, DIG. 23, 203/DIG. 21, 97, 1, 98, 99, DIG. 9, DIG. 19; 568/913, 918; 202/204; 560/218

[56] References Cited

U.S. PATENT DOCUMENTS

| | | | |
|---|---|---|---|
| 2,194,851 | 3/1940 | Guinot | 202/204 |
| 2,549,290 | 4/1951 | Congdon et al. | 203/DIG, 23 |
| 2,916,512 | 12/1959 | Fisher | 560/205 |
| 3,239,435 | 3/1966 | Conseilla et al. | 203/DIG. 23 |
| 3,337,740 | 8/1967 | Gray et al. | 203/DIG. 21 |
| 3,914,290 | 10/1975 | Otsuki et al. | 203/DIG. 21 |
| 3,951,756 | 4/1976 | Dirks et al. | 203/DIG. 21 |
| 4,464,229 | 8/1984 | Sato et al. | 203/DIG. 21 |
| 4,518,462 | 5/1985 | Aoshima et al. | 203/DIG. 21 |
| 4,698,440 | 10/1987 | Blair et al. | 203/DIG. 21 |
| 5,028,735 | 7/1991 | Segawa et al. | 203/83 |

FOREIGN PATENT DOCUMENTS

| | | | |
|---|---|---|---|
| 2832202 | 2/1979 | Germany | 203/DIG. 23 |
| 57-9740 | 1/1982 | Japan . | |
| 58-203940 | 11/1983 | Japan . | |

*Primary Examiner*—Virginia Manoharan
*Attorney, Agent, or Firm*—Cushman Darby & Cushman

[57] ABSTRACT

A distillation process is used to separate methanol from a mixture of methanol with methyl acrylate or methyl methacrylate, as well as from a mixture of methanol and water with methyl acrylate or methyl methacrylate with the use of an azeotropic solvent, which forms an azeotropic mixture with methanol. In distilling such a mixture by the use of a distillation column:

(1) part of the condensate of vapors distilled over from the top of the distillation column top is returned to the top of the column;
(2) the remaining condensate is separated into two layers;
(3) the upper layer essentially composed of an azeotropic solvent from the two separated layers is fed to an intermediate portion of the distillation column;
(4) the lower layer essentially composed of methanol from the above two separated layers is withdrawn from the distillation system; and
(5) methyl acrylate or methyl methacrylate, or else, methyl acrylate or methyl methacrylate and water, are recovered from the bottom of the column.

Water may be added to the remaining condensate at the time of separation into two layers. The amount of water added is 0.1–10 times the weight of methanol.

8 Claims, 4 Drawing Sheets

F I G. 2
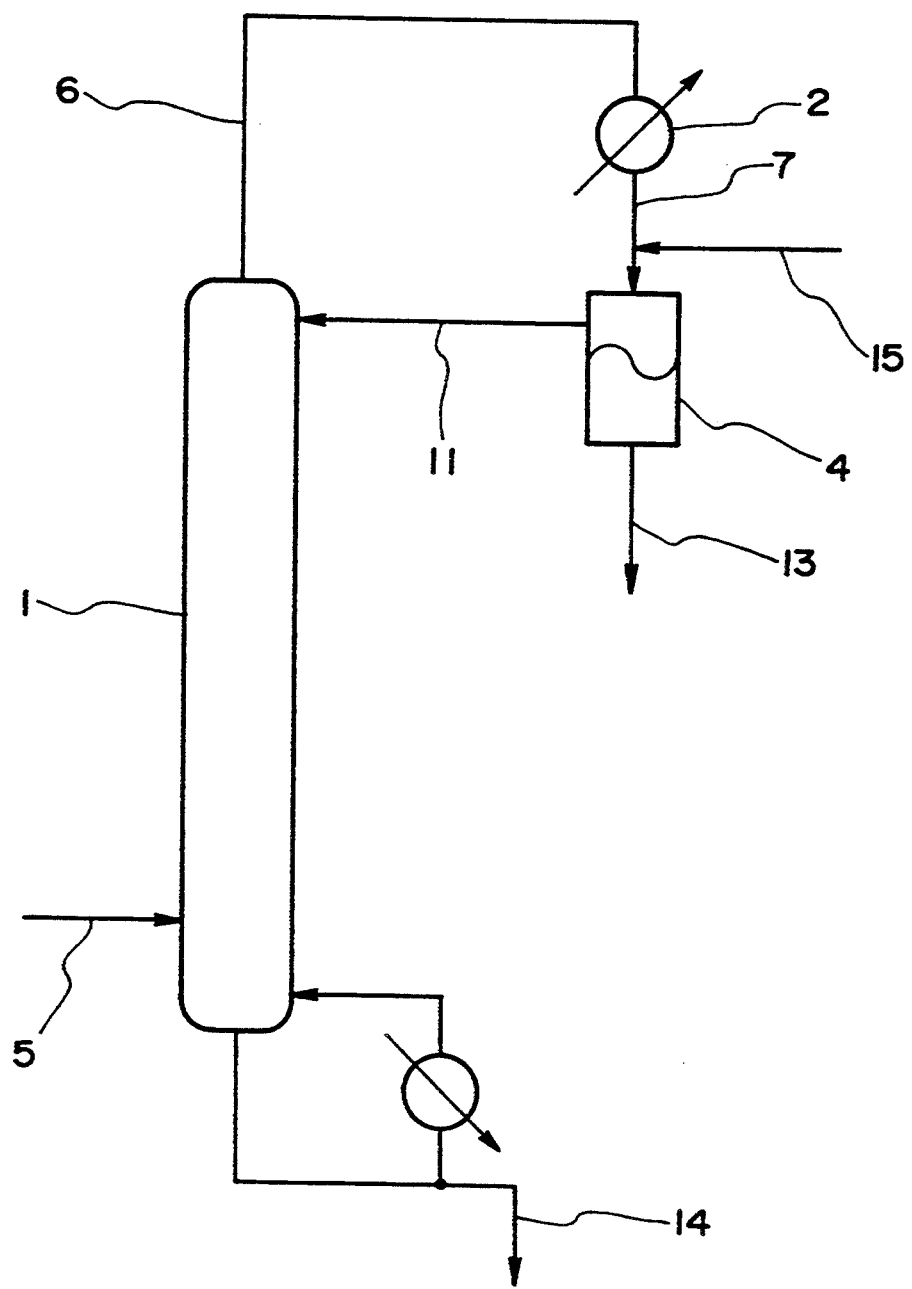

PROCESS FOR SEPARATING METHANOL AND METHYL ACRYLATE OR METHYL METHACRYLATE

BACKGROUND OF THE INVENTION

1. Field of the Invention

The present invention relates to a process for efficiently separating methanol from a mixture of methyl acrylate or methyl methacrylate with methanol. It also relates to a process for efficiently separating methanol from a mixture of methyl acrylate or methyl methacrylate with methanol and water. Hereafter, the term (meth)acrylic acid may be used to refer to either acrylic acid or methacrylic acid and the term methyl (meth)acrylate refers to either methyl acrylate or methyl methacrylate.

2. Description of the Related Art

It is known in the art that esterification of (meth)acrylic acid with methanol or ester exchange of an alcohol with methyl (meth)acrylate yields a mixture of methanol, methyl (meth)acrylate, and water.

The esterification reaction, which normally calls for an excess molar amount of methanol with respect to (meth)acrylic acid, essentially consumes all of the (meth)acrylic acid leaving no unreacted (meth)acrylic acid. Therefore, the liquid reaction mixture after the reaction is a liquid mixture comprising excess methanol, the reaction product methyl (meth)acrylate, and the reaction side product water.

The ester exchange reaction, which normally uses an excess molar amount of methyl (meth)acrylate with respect to an alcohol, consumes essentially all of the alcohol by the ester exchange reaction. Thus, the liquid reaction mixture after the reaction is a liquid mixture of the reaction side product methanol, unreacted methyl (meth)acrylate, and the reaction product ester. From among these components, the reaction product ester, which has a large boiling point difference from methanol and methyl (meth)acrylate, is relatively easy to separate, thereby providing a liquid mixture of the methanol and methyl (meth)acrylate free of the ester.

Several proposals have been made whereby an organic solvent capable of generating an azeotropic mixture with methanol is added to a mixture mainly comprising methyl (meth)acrylate and methanol, optionally containing water, followed by distilling to separate into methanol and methyl (meth)acrylate.

For example, a process is known in which a liquid mixture comprising methanol, water, and methyl (meth)acrylate is azeotropically distilled in the presence of an organic solvent and the entire amount of methanol is essentially stripped off the top of the distillation column and it is mostly free of water (see, e.g., U.S. Pat. No. 2,916,512; Japanese Laid-Open Publication 57-9740). The process, which strips off the methanol by azeotropic distillation, gives a distillate which contains the organic solvent. The process discloses that the distillate is fed to a decanter for separation into a layer mainly comprising the organic solvent and a layer mainly comprising methanol, and the organic solvent layer is returned to the distillation column. However, such a previously-known method, which efficiently distills and separates methanol from methyl (meth)acrylate, gives a distillate which still contains methyl (meth)acrylate, the distillate separating into two layers, with the lower layer mostly comprised of methanol mixed with methyl (meth)acrylate. Particularly, in the case of methyl acrylate, its low boiling point will give results in which the amount of contaminating methyl acrylate is more than negligible.

The esterification reaction recycles the separated methanol back to the reaction so that any contamination with methyl (meth)acrylate essentially poses no problem. However, the ester exchange reaction requires withdrawing out of the system the reaction by-product methanol, so that any methyl (meth)acrylate contained in the methanol gives rise to a recovery loss.

A proposal is given in Japanese Laid-Open Publication 57-9740 for reducing such recovery losses, which calls for controlling the type and amount of the organic solvent which forms an azeotropic mixture with methanol, and the number of plates for the methanol condensation section of the distillation column. The process, while exhibiting some effect, is still deficient in that the amount of methyl (meth)acrylate distillate cannot be substantially decreased. Japanese Laid-Open Publication 58-203940 teaches a process for recovering methanol, which comprises separating the distilled methanol and azeotropic solvent into two layers, feeding the upper layer mainly comprising the azeotropic solvent to the upper-most plate of the distillation column and feeding the lower layer, mostly comprised of methanol, into another distillation column (hereafter a second distillation column), recovering from the top of the second distillation column the azeotropic solvent that was dissolved in methanol, and recovering methanol from the bottom of the second distillation column. However, that process, which makes it possible to recover the azeotropic solvent, feeds a liquid mainly comprised of methanol to the second distillation column, where the contaminating methyl (meth)acrylate is not separated and contaminates the methanol which is recovered from the bottom of the second distillation column.

Such methanol before use in other applications must be freed of any impurities with boiling points higher than methanol by distillation so that any methyl (meth)acrylate contained in the methanol would be discarded with the impurities, creating a recovery loss and making the process deficient.

SUMMARY OF THE INVENTION

The primary object of the present invention is to overcome the above deficiencies. The present invention provides a process for recovering methanol using an azeotropic solvent from a mixture of methyl (meth)acrylate and methanol, sometimes containing water, which substantially reduces the amount of methyl (meth)acrylate contamination of methanol and which readily separates methanol from a distillation-separated liquid mixture of methanol and the azeotropic solvent.

The present invention is a process for separation by distillation of methanol from a mixture of methyl acrylate or methyl methacrylate and methanol, or a mixture of methyl acrylate or methyl methacrylate and methanol and water, using an azeotropic solvent that generates an azeotropic mixture with methanol, which comprises the distilling such a mixture by the use of a distillation column, further comprising the steps of:

(1) returning part of the condensate of vapors distilled over from the top of a distillation column to the top of the column;

(2) separating the remaining condensate into two layers;

(3) feeding the upper layer essentially comprising the azeotropic solvent, separated from the said two layers, to an intermediate portion of the distillation column;

(4) withdrawing the lower layer essentially comprised of methanol separated from the above two layers out of the distillation system; and (5) recovering from the bottom of the column methyl acrylate or methyl methacrylate, or methyl acrylate or methyl methacrylate and water, thereby separating methanol from methyl acrylate or methyl methacrylate, or methanol from methyl acrylate or methyl methacrylate and water.

BRIEF DESCRIPTION OF THE DRAWINGS

These and other features and advantages of the present invention will become better understood by making reference to the following description, attendant claims, and accompanying drawings.

FIG. 2 is a diagrammatic flow sheet for a type of apparatus used in accordance with prior art by a continuous process from a mixture of methyl (meth)acrylate and methanol: 1 . . . Distillation Column; 2 . . . Condenser; 4 . . . Decanter; and 5,6,7,13,14, and 15 . . . Delivery Tubes.

DESCRIPTION OF PREFERRED EMBODIMENTS

Figure 1:
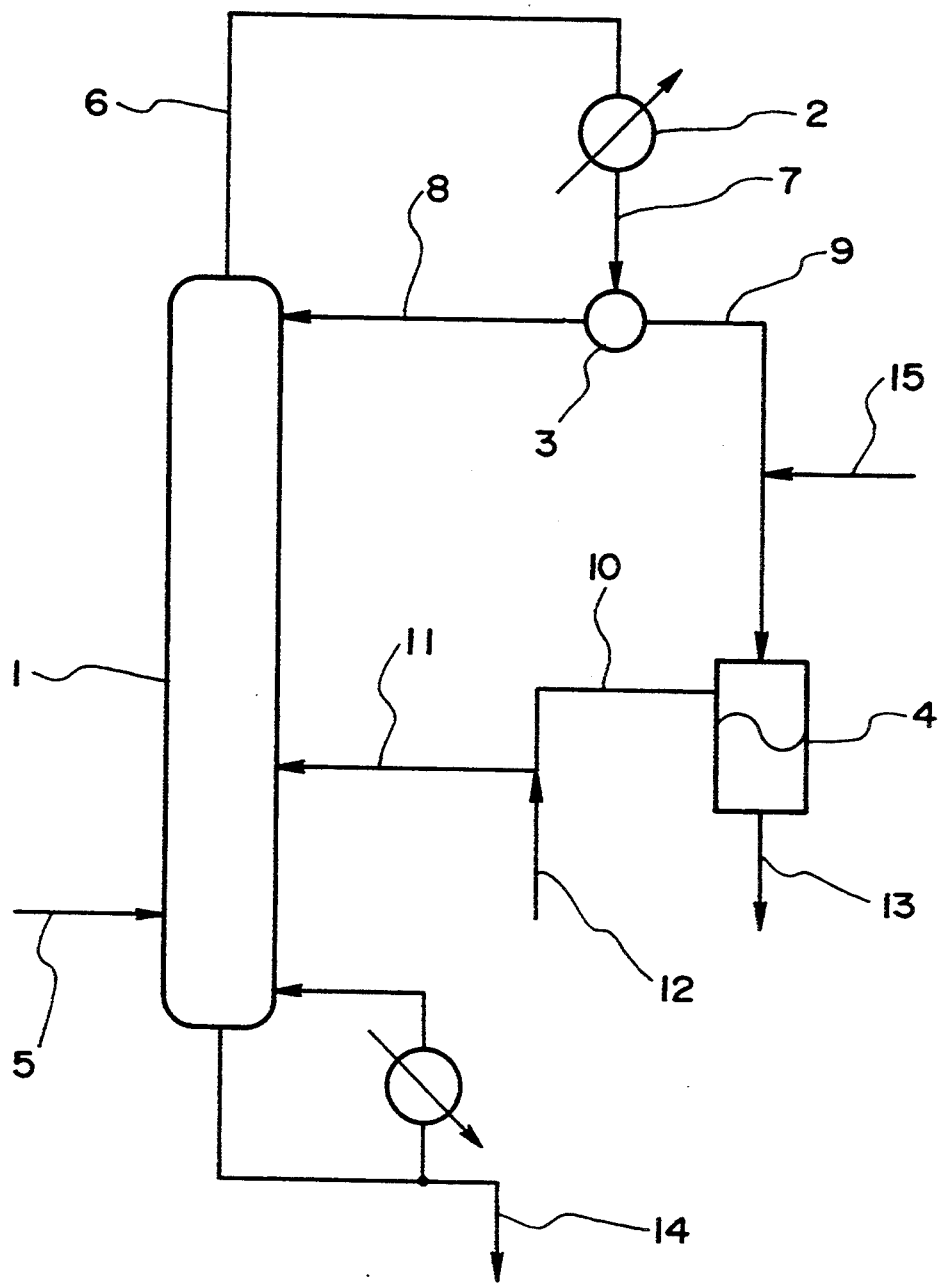
FIG. 1 is a diagrammatic flow sheet for one type of apparatus used for recovering methanol by a continuous process from a mixture of methyl (meth)acrylate and methanol in the process of the present invention: 1 . . . Distillation Column; 2 . . . Condenser; 3 . . . Liquid Distributor; 4 . . . Decanter; and 5,6,7,8,9,10,11,12,13,14, and 15 . . . Delivery Tubes.

The present invention uses azeotropic solvents capable of forming azeotropes with methanol, which are aliphatic saturated hydrocarbons, aliphatic unsaturated hydrocarbons, alicyclic hydrocarbons, organic halides, ethers, esters, and others.

Azeotropic solvents which may be used in this invention are required to have the following properties:

(1) to form a minimum azeotropic mixture with methanol boiling below the boiling point of methanol, with the azeotropic temperature as low as possible;

(2) to form no azeotropic mixture with methyl (meth)acrylate;

(3) to give an azeotropic mixture with methanol which is capable of forming two liquid layers on standing and of having the density difference substantial enough for separation; and (4) to undergo no chemical reaction during distillation with methanol or methyl (meth)acrylate.

Those which are provided with the above properties (1)–(4), have low cost, and are readily available are linear or branched aliphatic saturated hydrocarbons, preferably aliphatic saturated hydrocarbons with 5–8 carbon atoms, such as n-pentane, n-hexane, n-heptane, n-octane, 2,3-dimethylbutane, 2,5-dimethylhexane, 2,2,4-trimethylpentane, and the like. Table 1 lists the azeotropic temperatures and azeotropic compositions of methanol with these aliphatic saturated hydrocarbons.

TABLE 1

Azeotropic temperatures and azeotropic compositions of methanol with aliphatic unsaturated hydrocarbons (edited by Yuki Gosei Kagaku Kyokai [Organic Synthetic Chemical Association]: "Yozai Pocketbook" ["Solvent Pocketbook"], OHM Company, Japan, 1967)

| Aliphatic Saturated Hydrocarbons | Azeotropic Temperature | Azeotropic Composition |
|---|---|---|
| n-pentane | 30.8 | 91 |
| n-hexane | 50.6 | 72 |
| n-heptane | 59.1 | 48.5 |
| n-octane | 63.0 | 28 |
| 2,3-dimethylbutane | 45.0 | 80 |
| 2,5-dimethylhexane | 61.0 | 40 |
| 2,2,4-trimethylpentane | 59.4 | 47 |

NOTE: In the table, the azeotropic temperature refers to a temperature at 760 mmHg with the unit in °C.
NOTE: In the table, the azeotropic composition is by weight of organic solvents.

The present invention requires that the separation of methanol by distillation with an azeotropic solvent be carried out in such a manner that the top of the distillation column has an azeotropic composition of methanol and the azeotropic solvent.

In accordance with this invention, returning part of the condensate of mixed vapors of methanol and the azeotropic solvent distilled over from the top of the distillation column to the top of the distillation column, preferably in an amount of at least 15% by weight, more particularly at least 20% by weight of the condensate, makes it easy to maintain an azeotropic composition at the top of the column, which advantageously decreases the temperature of the top of the column, thereby preventing any methyl (meth)acrylate from distilling over. Returning part of the condensate to the top of the distillation column, may be carried out by first condensing the distillate and separating it into two layers, an upper layer essentially comprising the azeotropic solvent and a lower layer essentially comprising methanol, followed by returning the upper and lower layers at a flow ratio corresponding to the azeotropic composition, thereby achieving the same effect.

In order to decrease any loss in methyl (meth)acrylate by distilling over, it is preferred to operate and control the distillation column at least ten or more plate from the top of the distillation column, at a temperature essentially the same as the azeotropic temperature of the azeotropic compositional mixture of methanol and the azeotropic solvent. This operation and control can be carried out by adjusting the reflux ratio when returning part of the condensate.

The above-mentioned related art comprises separating the distillate into two layers and then returning only the upper layer mainly comprised of an azeotropic solvent. That is a sensible operation from the standpoint of removing methanol, but such a method will result in a distillate extensively contaminated with methyl (meth)acrylate. The reason for this, although not completely understood, may be that the contamination is caused by the liquid composition at the top of the column deviating from the azeotropic composition, resulting in an increased temperature, which in turn, increases the amount of methyl (meth)acrylate distilling over.

After returning part of the distillate in this invention, the remaining condensate, mainly comprising a mixture of methanol and azeotropic solvent, is then allowed to separate into two layers: the upper layer is essentially comprised of the azeotropic solvent and the lower is essentially comprised of methanol.

The upper layer is returned to an intermediate portion of the distillation column, preferably to a portion of the column where the azeotropic solvent concentration is highest; the portion at which the azeotropic solvent concentration is the highest in the column differs depending upon the number of plates of the column and the amount of the azeotropic solvent present.

The lower layer essentially comprised of methanol is then withdrawn out of the distillation system, but depending upon the type of azeotropic solvent, there may be cases in which the separation into two layers, methanol and the azeotropic solvent, is not easy or the mutual solubility of the components may be high even if a two-layer separation is achieved, resulting in a lower layer which contains a substantial amount of the azeotropic solvent. The recovering and recycling of methanol and the azeotropic solvent in such cases requires separating the two, where a method may be used to employ a second distillation column for that purpose, so as to recover from the top of the column the azeotropic solvent which is dissolved in methanol and to recover methanol from the bottom of the column. In this case, the lower layer liquid mainly comprised of methanol which is led to the second distillation column is not contaminated with methyl (meth)acrylate so that the methanol recovered in the second distillation column is free of methyl (meth)acrylate. This method is effective when recovering and recycling methanol in a large scale unit, or the like.

However, having a second distillation column is too costly in capital investment to be preferred merely for reducing the loss of an azeotropic solvent in the case of a small-scale unit, where methanol recovery is not economical and methanol is disposed of by incineration. In such a case where there is no need for methanol recovery and capital costs should be reduced as much as possible, water may be added to the condensate, which is the azeotropic mixture remaining after being partially returned to the top of the distillation column, so as to facilitate a two-layer separation into methanol and the azeotropic solvent and also to substantially decrease the concentration of the azeotropic solvent in the methanol.

The latter method which does not require a second distillation column, but involves adding only water, can remove methanol essentially free of any azeotropic solvent from a mixed liquid of methanol and an azeotropic solvent, minimizing the loss of the azeotropic solvent. This method is suitably used, particularly in a small-scale unit for the separation of methyl acrylate and methanol.

The amount of water added by weight is 0.1–10 times, preferably 0.5–5 times the weight of methanol, where the methanol is recovered in the form of an aqueous methanol solution, and is then withdrawn out of the distillation system.

In this manner, removal of methanol permits recovering methyl (meth)acrylate from the bottom of the column. If the feed to the distillation column comprises methyl (meth)acrylate, methanol and water, both methyl (meth)acrylate and water are recovered from the bottom of the column.

Thus, even if water may be present in a liquid mixture of methyl (meth)acrylate and methanol, distillation with an azeotropic solvent permits discharging water together with methyl (meth)acrylate from the bottom of the column, so that whether or not water is present in the feed to the distillation column essentially does not affect the extent of loss of methyl (meth)acrylate into the methanol.

The embodiment of this invention as described above is now explained by referring to the attached drawing (FIG. 1). It should be noted that the present invention is not limited to an embodiment depicted in FIG. 1.

A mixture of methanol and methyl (meth)acrylate is fed through delivery tube 5 and is distilled in distillation column 1. Essentially methanol-free methyl (meth)acrylate is recovered through delivery tube 14 from the bottom of distillation column 1. Methanol and the azeotropic solvent are stripped as azeotropic mixed vapors and are led through delivery tube 6 and condensed by condenser 2 to give a condensate, which is then led through delivery tube 7 into liquid distributor 3. The liquid distributor separates the mixture of methanol and the azeotropic solvent into two parts. Part of the condensate is led through delivery tube 8 and returned to the top of distillation column 1, while the remaining part of the condensate is led through delivery tube 9 into decanter 4. Whether or not the amounts of liquid distributed by the liquid distributor 3 are optimum can be readily judged by a variation in the number of plates with respect to the azeotropic composition of distillation column 1, but the liquid distribution ratio can also be set up by using the following Equation (I):

$$\frac{W_T}{W_V} = 1 - (p/q)(1 + r)(W_F/W_V) \qquad (I)$$

wherein $W_T$, $W_V$, $W_F$, p, q, and r are defined as follows:

$W_T$: rate of condensate distributed from liquid distributor 3 to the top of distillation column (g/hr);

$W_V$: rate of condensate condensed by passage through delivery tube 6 in condenser 2 (g/hr);

$W_F$: rate of liquid (g/hr) of a mixture of methanol and methyl (meth)acrylate fed through delivery tube 5 to the distillation column 1.

p: methanol concentration in mixture $W_F$ fed from the delivery tube 5 to the distillation column 1;

q: methanol concentration in an azeotropic mixture of azeotropic solvent and methanol;

$$r: \frac{\text{Rate of methanol(g/hr) in the upper layer from } (W_V - W_T)}{pW_F}$$

[where the upper layer from ($W_V$-$W_T$) is fed to the intermediate portion of the distillation column]

Decanter 4 performs layer separation, and the upper layer, which is mainly comprised of the azeotropic solvent, is fed from delivery tube 10 through delivery tube 11 into the intermediate part of distillation column 1, and the lower layer mainly comprised of methanol is allowed to flow through delivery tube 13 out of the distillation system.

If the mixture of methanol and methyl (meth)acrylate which is fed from delivery tube 5 contains water, essentially methanol-free methyl (meth)acrylate and water are recovered through delivery tube 14 from the bottom of distillation column 1. As described above, if water is added to the condensate remaining after partially returning to the top of the distillation column, in order to facilitate a two-layer separation in decanter 4, the water is then fed through delivery tube 15 into decanter 4. In this case, an aqueous methanol solution is allowed to flow out of delivery tube 13.

The azeotropic solvent for replenishing is fed through delivery tube 12 into distillation column 1.

Figure 3:
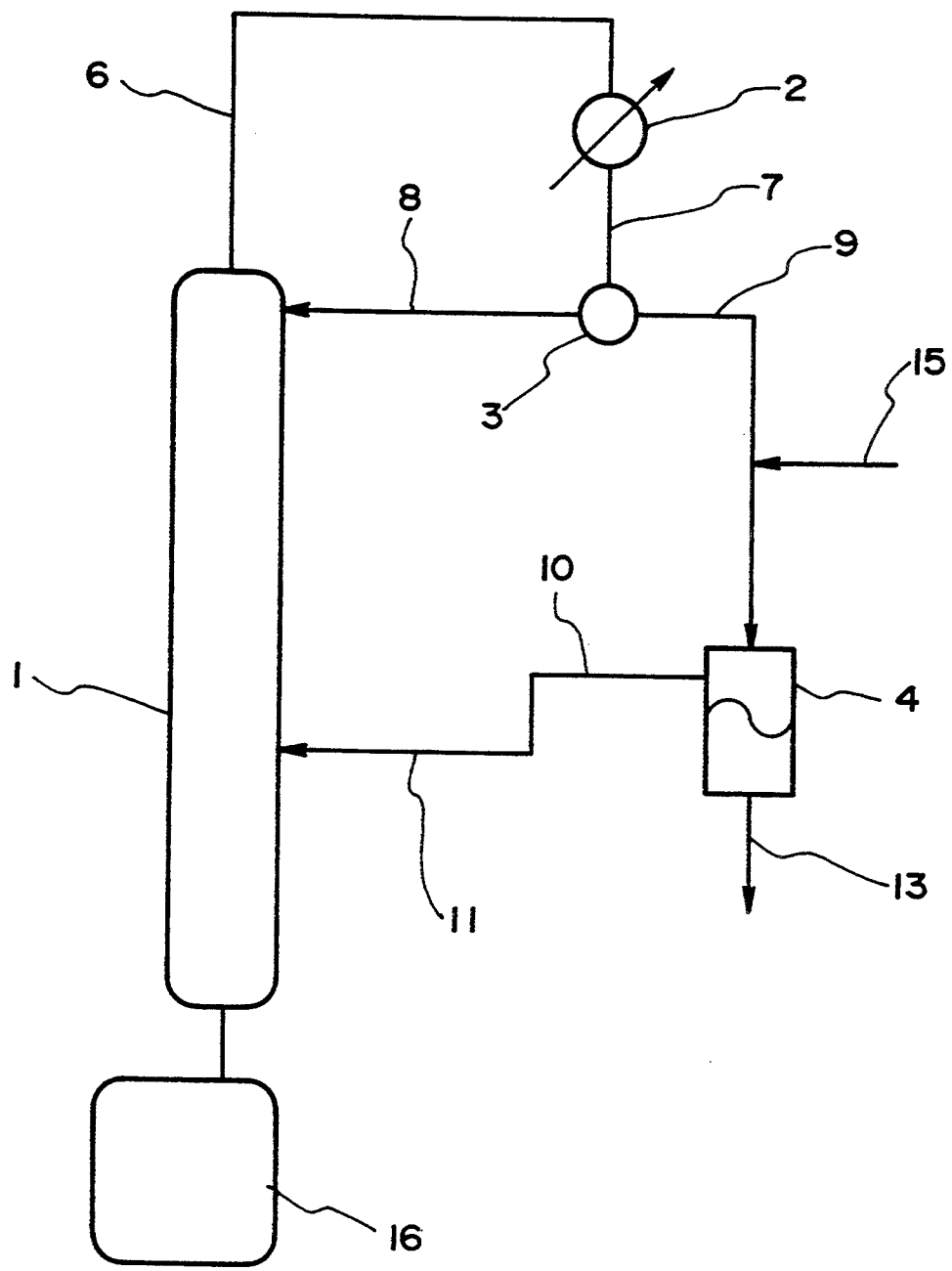
FIG. 3 is a diagrammatic flow sheet showing an ester exchange reactor equipped with a distillation column used in an embodiment of this invention: 1 . . . Distillation Column; 2 . . . Condenser; 3 . . . Liquid Distributor; 4 . . . Decanter; 6,7,8,9,10,11,13, and 15 . . . Delivery Tubes; and 16 . . . Ester Exchange Reactor.

As illustrated in FIG. 1, the present invention can be suitably used for recovering methanol by a continuous process from a mixture of methyl (meth)acrylate with methanol optionally containing water. However, as illustrated in FIG. 3, this invention can also be suitably used to strip off, with essentially no loss of methyl (meth)acrylate, the methanol which is formed in ester exchange reactor 16 that is provided with distillation column 1.

The present invention can be carried out either at atmospheric pressure or at reduced pressure.

EXAMPLES

The present invention is further explained in detail by the following examples. However, these examples in no way limit the scope of this invention. In these examples, percent is based on weight.

EXAMPLE 1

An experiment was carried out using an apparatus shown in FIG. 1. Use was made of an i.d. 35 mm, 30-plate Oldershaw column as the distillation column and n-hexane as an azeotropic solvent. Distillation was carried out at atmospheric pressure.

An azeotropic mixture (containing 54% methanol) of methyl acrylate and methanol was fed through delivery tube 5 at a rate of 117.4 g/hr to the 25th plate from the top of the distillation column 1, while 99.50% pure methyl acrylate was withdrawn at a rate of 53.59 g/hr from the bottom of the column through delivery tube 14.

Vapors distilling off the top of the column were led through delivery tube 6 and cooled in condenser 2 (with the use of a −10° C. refrigerant) to give a condensate, which was then led through delivery tube 7 at a rate of about 400 g/hr into liquid distributor 3. Liquid distributor 3 was operated to return part of the condensate through delivery tube 8 to the top of the distillation column in such a manner that the temperature from the top of the column to the 15th plate was held at 50.6° C. and the remaining condensate was fed through delivery tube 9 to decanter 4. The distribution of the condensate for the column top:decanter was equal to about 2:3. The condensate led to decanter 4 was separated into two layers in decanter 4 and the upper layer of decanter 4 was introduced from delivery tube 10 through delivery tube 11 into the 20th plate from the top of the column, while the lower layer of decanter 4 was withdrawn through delivery tube 13, with the liquid level in the separated layers within the decanter held constant. Water was at the same time fed to the decanter 4 through delivery tube 15 at a rate of 168.0 g/hr.

In this case, the lower layer of decanter 4 provided 231.8 g/hr of methanol containing 0.003% of n-hexane, 0.29% of methyl acrylate, and 72.47% of water. The methyl acrylate recovery loss amounted to 1.26%.

EXAMPLE 2

An experiment was carried out using an apparatus shown in FIG. 1. Use was made of an i.d. 35 mm, 30-plate Oldershaw column as the distillation column and n-hexane as an azeotropic solvent. Distillation was carried out at atmospheric pressure.

An azeotropic mixture (containing 54% methanol) of methyl acrylate and methanol was fed through delivery tube 5 at a rate of 121.0 g/hr to the 25th plate from the top of the distillation column 1, while 99.36% pure methyl acrylate was withdrawn at a rate of 54.43 g/hr from the bottom of the column through delivery tube 14.

Vapors distilling off the top of the column were led through delivery tube 6 and cooled in condenser 2 (with the use of a −10° C. refrigerant) to give a condensate, which was then led through delivery tube 7 at a rate of about 385 g/hr into liquid distributor 3. Liquid distributor 3 was operated to return part of the condensate through delivery tube 8 to the top of the distillation column in such a manner that the temperature from the top of the column to the 15th plate was held at 50.6° C. and the remaining condensate was fed through delivery tube 9 to decanter 4. The distribution of the condensate for the column top:decanter was equal to about 1:3. The condensate fed to decanter 4 was separated into two layers in decanter 4 and the upper layer of decanter 4 was introduced from delivery tube 10 through delivery tube 11 into the 20th plate from the top of the column, while the lower layer of decanter 4 was withdrawn through delivery tube 13, with the liquid level in the separated layers within the decanter held constant. In this case, the lower layer of decanter 4 provided 98.04 g/hr of methanol containing 32.47% of n-hexane and 1.61% of methyl acrylate. The methyl acrylate recovery loss amounted to 2.84%.

COMPARATIVE EXAMPLE 1

An experiment was carried out using an apparatus shown in FIG. 2. Use was made of an i.d. 35 mm, 30-plate Oldershaw column as the distillation column and the n-hexane was an azeotropic solvent. Distillation was carried out at atmospheric pressure.

An azeotropic mixture (containing 54% methanol) of methyl acrylate and methanol was fed at a rate of 118.0 g/hr through delivery tube 5 to the 20th plate counting from the top of the distillation column 1, and 99.37% pure methyl acrylate was withdrawn from the bottom of the column through delivery tube 14 at a rate of 43.07 g/hr.

Vapors stripped off the top of the column were led through delivery tube 6 and cooled in condenser 2 (with the use of a −10° C. refrigerant) to give a condensate which was then led through delivery tube 7 directly to decanter 4. The condensate introduced into decanter 4 was separated into two layers in decanter 4 followed by feeding the upper layer from decanter 4 through delivery tube 11 to the top of the column while the lower layer of decanter 4 was withdrawn through delivery tube 13 with the liquid levels of the separated layers within decanter 4 held constant. Water was at the same time fed to decanter 4 through delivery tube 15 at a rate of 155.0 g/hr.

The lower layer of decanter 4 gave 229.95 g/hr of methanol containing 0.007% of n-hexane, 4.99% of methyl acrylate, and 67.41% of water. The methyl acrylate recovery loss amounted to 21.15%.

COMPARATIVE EXAMPLE 2

Comparative Example 1 was repeated for this experiment except for feeding no water to decanter 4. Immediately after starting to return the upper layer of decanter 4 to the top of the column, the material in decanter 4 became a homogeneous layer.

EXAMPLE 3

An experiment was carried out using an apparatus shown in FIG. 1. Use was made of an i.d. 35 mm, 30-plate Oldershaw column as the distillation column and n-hexane as an azeotropic solvent. Distillation was carried out at atmospheric pressure.

An azeotropic mixture (containing 82% methanol) of methyl methacrylate and methanol was fed through delivery tube 5 at a rate of 78.1 g/hr to the 25th plate from the top of the distillation column 1, while 14.09 g/hr of 99.80% pure methyl methacrylate was withdrawn from the bottom of the column through delivery tube 14.

Vapors distilling off the top of the column were led through delivery tube 6 and cooled in condenser 2 (with the use of a $-10°$ C. refrigerant) to give a condensate, which was then led through delivery tube 7 at a rate of about 450 g/hr into liquid distributor 3. Liquid distributor 3 was operated to return part of the condensate through delivery tube 8 to the top of the distillation column in such a manner that the temperature from the top of the column to the 15th plate was held at 50.6° C. and the remaining condensate was led through delivery tube 9 to decanter 4. The distribution of the condensate for the column top:decanter was equal to about 1:1.2. The condensate led to decanter 4 was separated into two layers in decanter 4 and the upper layer of decanter 4 was introduced from delivery tube 10 through delivery tube 11 into the 20th plate from the top of the column, while the lower layer of decanter 4 was withdrawn through delivery tube 13, with the liquid level in the separated layers within the decanter held constant. Water was at the same time fed to decanter 4 through delivery tube 15 at a rate of 168.0 g/hr.

In this case, the lower layer of decanter 4 provided 232.1 g/hr of methanol containing 0.002% of n-hexane and 70.4% of water. The lower layer had no detectable methyl methacrylate.

EXAMPLE 4

An experiment was carried out by repeating Example 3, except for feeding no water to decanter 4. The lower layer in decanter 4 showed no detectable methyl methacrylate.

COMPARATIVE EXAMPLE 3

An experiment was carried out using an apparatus shown in FIG. 2. Use was made of an i.d. 35 mm, 30-plate Oldershaw column as the distillation column and the n-hexane was an azeotropic solvent. Distillation was carried out at atmospheric pressure.

An azeotropic mixture (containing 82% methanol) of methyl methacrylate and methanol was fed at a rate of 81.5 g/hr through delivery tube 5 to the 20th plate counting from the top of the distillation column 1 and withdrawing from the bottom of the column, 99.45% pure methyl methacrylate through delivery tube 14 at a rate of 14.49 g/hr.

Vapors stripped off the top of the column were led through delivery tube 6 and cooled in condenser 2 (with the use of a $-10°$ C. refrigerant) to give a condensate which was then fed through delivery tube 7 directly to decanter 4. The condensate introduced into decanter 4 was separated into two layers in decanter 4 followed by feeding the upper layer from decanter 4 through delivery tube 11 to the top of the column while the lower layer of decanter 4 was withdrawn through delivery tube 13 with the liquid levels of the separated layers within decanter 4 held constant. Water was at the same time fed to decanter 4 through delivery tube 15 at a rate of 176.0 g/hr.

The lower layer of decanter 4 gave 243.0 g/hr of methanol containing 0.007% of n-hexane, 0.11% of methyl methacrylate, and 72.42% of water. The methyl methacrylate recovery loss amounted to 1.77%.

COMPARATIVE EXAMPLE 4

An experiment was carried out using an apparatus shown in FIG. 2. Use was made of an i.d. 35 mm, 30-plate Oldershaw column as the distillation column and the n-hexane was an azeotropic solvent. Distillation was carried out at atmospheric pressure.

An azeotropic mixture (containing 82% methanol) of methyl methacrylate and methanol was fed at a rate of 76.6 g/hr through delivery tube 5 to the 25th plate counting from the top of the distillation column 1, and 99.78% pure methyl methacrylate was withdrawn from the bottom of the column through delivery tube 14 at a rate of 13.52 g/hr.

Vapors stripped off the top of the column were led through delivery tube 6 and cooled in condenser 2 (with the use of a $-10°$ C. refrigerant) to give a condensate which was then fed through delivery tube 7 directly to decanter 4. The condensate introduced into decanter 4 was separated into two layers in decanter 4 followed by feeding the upper layer from decanter 4 through delivery tube 11 to the top of the column while the lower layer of decanter 4 was withdrawn through delivery tube 13 with the liquid levels of the separated layers within decanter 4 held constant. The lower layer of decanter 4 gave 69.09 g/hr of methanol containing 8.7% of n-hexane, and 0.44% of methyl methacrylate. The methyl methacrylate recovery loss amounted to 2.2%.

EXAMPLE 5

An experiment was carried out using an apparatus shown in FIG. 3. Use was made of an i.d. 35 mm, 30-plate Oldershaw column as the distillation column and a 2-L flask as an ester exchange reactor. The azeotropic solvent was n-hexane.

Ester exchange reactor 16 was charged with 998 g of methyl acrylate, 552 g of dimethyl aminoethanol, 22 g of dibutyltin oxide, and 1.76 g of phenothiazine so as to carry out a reaction at atmospheric pressure.

Vapors stripped from the top of distillation column 1 were led through delivery tube 6 and cooled in condenser 2 (with the use of a $-10°$ C. refrigerant) to give a condensate which was then led through delivery tube 7 into liquid distributor 3. Liquid distributor 3 was operated to return part of the condensate through delivery tube 8 to the top of the distillation column so as to maintain the temperatures from the column top to the 15th plate at 50.6° C. and the remaining condensate liquid was led through delivery tube 9 to decanter 4. The condensate led to decanter 4 was separated into two layers in decanter 4. The upper layer of decanter 4 was fed from delivery tube 10 to delivery tube 11 to the 20th plate counting from the top of the column, while the lower layer from decanter 4 was discharged through delivery tube 13, while the liquid levels in the separated layers within the decanter 4 were maintained constant. Water was at the same time fed to the decanter 4 through delivery tube 15 at a rate of 80 g/hr. Reactor 16 was fed with 22 g/hr of methyl acrylate.

The reaction was completed in 8.5 hours, resulting in the ester exchange reactor 16 having a reaction liquid mixture containing 841 g of dimethylaminoethyl acrylate. The distillate from decanter 4 was 873.4 g of methanol containing 0.002% of n-hexane, 0.23% of methyl acrylate, and 77.9% of water. The methyl acrylate loss amounted to 0.17%.

COMPARATIVE EXAMPLE 5

Figure 4:
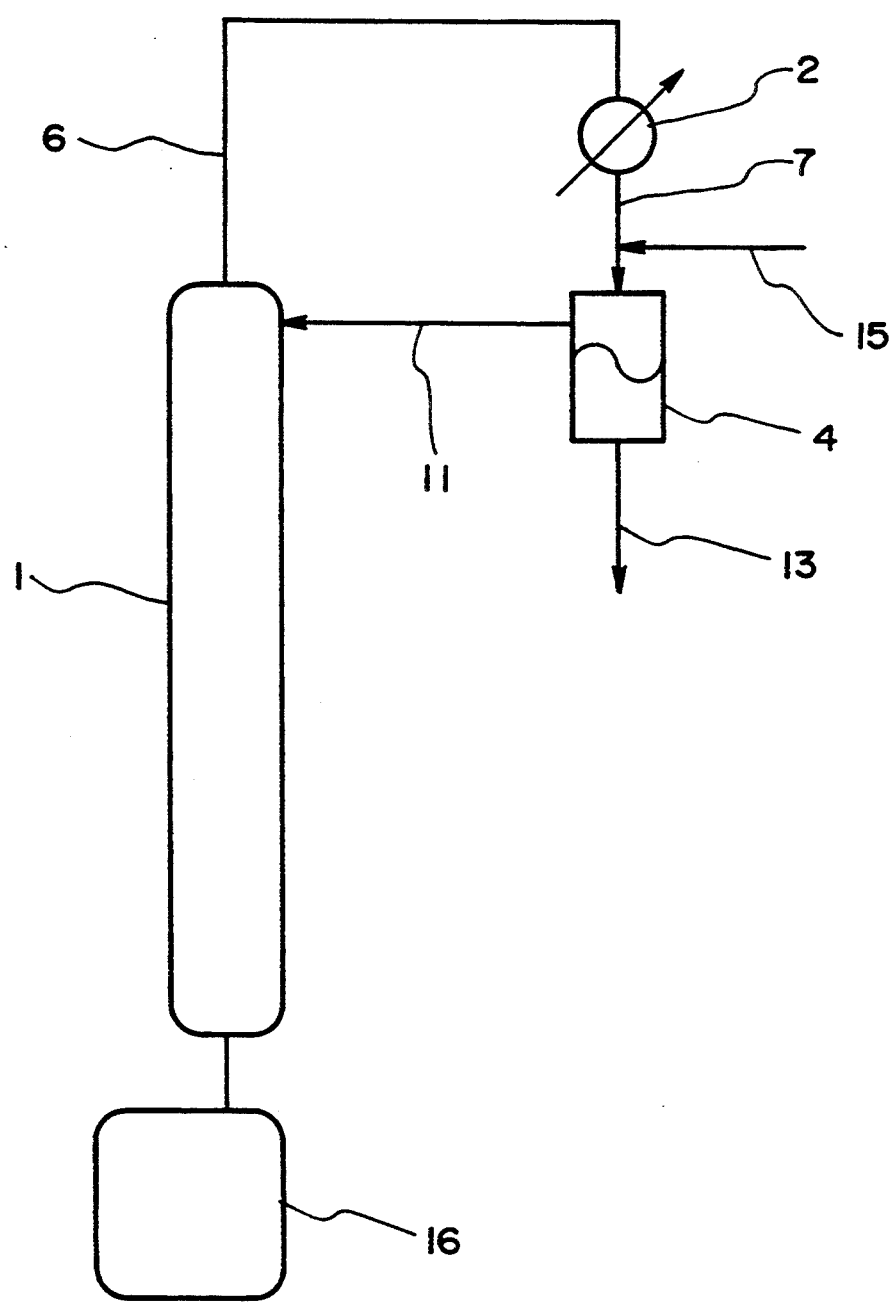
FIG. 4 is a diagrammatic flow sheet showing an ester exchange reactor equipped with a distillation column used in prior art: 1 . . . Distillation Column; 2 . . . Condenser; 4 . . . Decanter; 6,7,11,13, and 15 . . . Delivery Tubes; and 16 . . . Ester Exchange Reactor.

An experiment was carried out using an apparatus shown in FIG. 4. Use was made of an i.d. 35 mm, 30-plate Oldershaw column as the distillation column and a 2-L flask as an ester exchange reactor. The azeotropic solvent was n-hexane.

Ester exchange reactor 16 was charged with 998 g of methyl acrylate, 552 g of dimethyl aminoethanol, 22 g of dibutyltin oxide, and 1.76 g of phenothiazine so as to carry out a reaction at atmospheric pressure.

Vapors stripped from the top of distillation column 1 were led through delivery tube 6 and cooled in condenser 2 (with the use of a −10° C. refrigerant) to give a condensate which was then led through delivery tube 7 directly into decanter 4. The condensate led to decanter 4 was separated into two layers in decanter 4 and the upper layer of decanter 4 was fed through delivery tube 11 to the top of the column, while the lower layer from decanter 4 was discharged through delivery tube 13, with the liquid levels in the separated layers within the decanter 4 held constant. Water was fed at the same time to decanter 4 through delivery tube 15 at a rate of 80 g/hr.

The reaction was completed in 8.5 hours, resulting in the ester exchange reactor 16 having a reaction liquid mixture containing 841 g of dimethylaminoethyl acrylate. The distillate from decanter 4 was 906.0 g of methanol containing 0.002% of n-hexane, 3.81% of methyl acrylate, and 75.1% of water. The methyl acrylate recovery loss amounted to 2.91%.

As described above, the present invention can separate methanol by distillation from a mixture of methyl (meth)acrylate and methanol with essentially no loss of methyl (meth)acrylate. The addition of water to a distillate mixture of methanol and the azeotropic solvent permits an efficient separation of methanol from the azeotropic solvent without the use of a second distillation column, giving a substantial economic advantage.

What is claimed is:

1. A process for separation by distillation of methanol from a starting mixture of methyl acrylate or methyl methacrylate, and methanol, or a starting mixture of methyl acrylate or methyl methacrylate, methanol and water, using an azeotropic solvent that generates an azeotropic mixture with methanol, which comprises:
   (1) distilling the starting mixture by the use of a distillation column having a top and a bottom,
   (2) condensing vapors distilled over from the top of the distillation column to produce a condensate;
   (3) returning a first portion of the condensate in an amount of at least 15% by weight to the top of the distillation column, said returning including adjusting a reflux ratio;
   (4) separating a remaining portion of the condensate into upper and lower layers;
   (5) separating the upper layer comprising the azeotropic solvent, and feeding the upper layer to an intermediate portion of the distillation column;
   (6) separating the lower layer comprising methanol essentially free of methyl acrylate or methyl methacrylate and withdrawing the lower layer out of the distillation system; and
   (7) recovering from the bottom of the column methyl acrylate or methyl methacrylate, or, recovering methyl acrylate or methyl methacrylate, and water, thereby separating methanol from methyl acrylate or methyl methacrylate, or separating methanol from methyl acrylate or methyl methacrylate, and water.

2. A process for separation as set forth in claim 1 during the step of separating the remaining portion of the condensate into two layers, water is added to facilitate separation.

3. A process for separation as set forth in claim 2 wherein the amount of water added is 0.1–10 times the weight of methanol.

4. A process for separation as set forth in claim 2 wherein the amount of water added is 0.5–5 times the weight of methanol.

5. A process for separation as set forth in claim 1 wherein the starting mixture comprises methyl acrylate and methanol.

6. A process for separation as set forth in claim 2 wherein the starting mixture comprises methyl acrylate and methanol.

7. A process for separation as set forth in claim 3 wherein the starting mixture comprises methyl acrylate and methanol.

8. A process for separation as set forth in claim 4 wherein the starting mixture comprises methyl acrylate and methanol.

* * * * *